United States Patent

Tafesh et al.

[11] Patent Number: 6,150,298
[45] Date of Patent: Nov. 21, 2000

[54] PROCESS FOR TELOMERIZING DIENES

[75] Inventors: Ahmed Tafesh, Acre, Israel; Matthias Beller, Rostock; Jochen Krause, Frankfurt, both of Germany

[73] Assignee: Celanese GmbH, Frankfurt, Germany

[21] Appl. No.: 09/242,918

[22] PCT Filed: Aug. 18, 1997

[86] PCT No.: PCT/EP97/04500

§ 371 Date: Jun. 25, 1999

§ 102(e) Date: Jun. 25, 1999

[87] PCT Pub. No.: WO98/08794

PCT Pub. Date: Mar. 5, 1998

[30] Foreign Application Priority Data

Aug. 27, 1996 [DE] Germany ............... 196 34 469

[51] Int. Cl.$^7$ .................................................. B01J 31/00
[52] U.S. Cl. ...................... 502/166; 502/156; 568/840
[58] Field of Search ...................... 502/166, 156, 502/162; 568/840

[56] References Cited

U.S. PATENT DOCUMENTS

| 4,142,060 | 2/1979 | Kuntz | 568/840 |
| 4,356,333 | 10/1982 | Yoshimura et al. | 568/840 |
| 5,118,885 | 6/1992 | Tokitoh et al. | 568/909.5 |
| 5,345,007 | 9/1994 | Monflier et al. | 568/909.5 |
| 5,565,398 | 10/1996 | Herrmann et al. | 502/166 |
| 5,736,480 | 4/1998 | Davis et al. | 502/155 |

FOREIGN PATENT DOCUMENTS

| 0 436 226 A1 | 7/1991 | European Pat. Off. |
| 0 571 819 A1 | 12/1993 | European Pat. Off. |
| 2 093 025 | 8/1982 | United Kingdom. |
| WO 95/30636 | 11/1995 | WIPO. |

OTHER PUBLICATIONS

P. N. Rylander: "Organic Syntheses with Noble Metal Catalysts Oligomerizats, Telomerizations & Condensat.", 1973. Derwent Publication, Week 9401, Dec. 15, 1992.

Primary Examiner—Ardin H. Marschel
Assistant Examiner—Sherif Kafafi
Attorney, Agent, or Firm—Frommer Lawrence & Haug LLP

[57] ABSTRACT

Process for the telomerization of dienes

The present invention relates to a process for the telomerization of dienes, according to which the diene is reacted with a compound containing an active hydrogen atom in the presence of a palladium compound, a water-soluble phosphine ligand and a base, the water-soluble ligand being a bidentate ligand having the following formula I

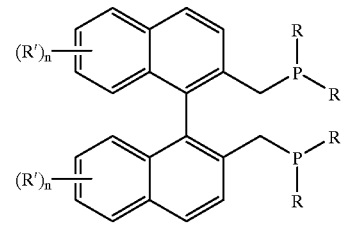

in which R is identical or different and is phenyl, $C_1$–$C_{12}$-alkyl or $C_3$–$C_{10}$-cycloalkyl, which may be unsubstituted or substituted by one or more radicals R', R' is identical or different and is $SO_3^-M^+$, —$NMe_3^+$ or —$COO^-M^+$, n is an integer from 1 to 6, in each case based on a naphthyl backbone, and M is H, Na, K, Cs or R"$_4$N$^+$ where R" is identical or different and is H, $C_1$–$C_{12}$-alkyl or $C_1$–$C_{10}$-cycloalkyl.

21 Claims, No Drawings

PROCESS FOR TELOMERIZING DIENES

DESCRIPTION

Process for the telomerization of dienes

The present invention relates to a process for the telomerization of dienes. In particular, the present invention relates to a process, according to which the diene is reacted in the presence of a bidentate phosphine ligand and a palladium compound to give the corresponding dimer. The process according to the invention gives the desired dimer in large yield and high selectivity.

PRIOR ART

The telomerization of ethylenically unsaturated compounds, such as, for example, dienes, can be used to obtain low molecular weight oligomers of these compounds, which are useful starting materials for the synthesis.

For example, the telomerization of dienes such as butadiene can be used to prepare the corresponding dimers. Butadiene in particular has attracted a lot of attention since it is readily obtainable at low cost and can be used for many purposes.

For example, it is known that butadiene can be reacted with alcohols (Takahashi, S. Shibano, T. Hagihara, N.; Bull. Chem. Soc. Japan. 1968, 41, 454 (b) Tetrahedron Letter. 1967, 2451), phenol (Smutny, E. J.; J. Am. Chem. Soc. 1967, 89, 6793), carboxylic acids (Manyik, R. M. Walker, W. E. Atkins, K. E.; Chemical Communication, 1971, 330), water (Tsuji, J. Takahashi, M.; J. Molec. Catalysis. 1981, 10, 107), ammonia (Tsuji, J. Mori, Y.; Tetrahedron. 1972, 28, 3721) and carbon monoxide (Kohle, J. F. Slaugh, L. H. Nakamaye, K. L.; J. Am. Chem. Soc. 1969, 91, 5904) to give the corresponding octadienyl ethers, esters, alcohols, amines and carboxylic acids.

These reactions, referred as to as telomerization, usually take place in the presence of a catalyst system comprising a transition metal compound and a complex ligand. Known transition metal compounds are palladium compounds, and known complex ligands are monodentate phosphine ligands.

For example, the reaction of butadiene with water in the presence of a palladium catalyst is an elegant method for the preparation of 2,7-octadienol. 2,7-Octadienol is an important intermediate for the synthesis of di-n-octyl phthalate, which is a plasticizer of industrial importance. The synthesis proceeds via the hydrogenation of 2,7-octadienol to give 1-octanol, which is reacted with phthalic anhydride to give di-n-octyl phthalate (see FIG. 1).

Figure I

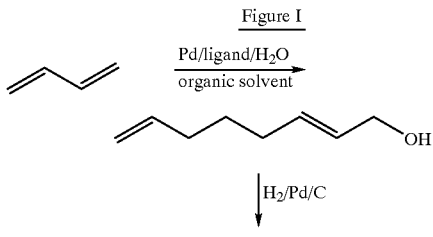

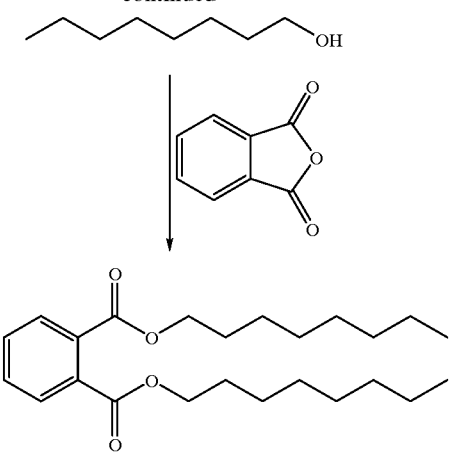

For example, U.S. Pat. No. 4,356,333 describes a process for the telomerization of butadiene with water (hydrodimerization), the reaction of the butadiene with water taking place in an aqueous sulfolane solution in the presence of palladium or a palladium compound, a water-soluble monodentate phosphine ligand and an amine compound having a base constant pKa=7 or higher.

In view of its low cost and good solubility properties, triethylamine is a particularly preferred amine compound. In addition, it has been found that merely replacing triethylamine with tri-n-propylamine results in a reduction in the octadienyl yield.

In addition, in the case of the process described here, the reaction rate drops considerably when the content of sulfolane is less than 30% by mass. If, on the other hand, the sulfolane content exceeds 80% by mass, then the extraction efficiency of 2,7-octadienol from the reaction mixture is impaired. The above process has the disadvantage that as well as requiring an amine compound, it additionally requires an organic solvent, namely sulfolane, which complicates the process, in particular product isolation.

U.S. Pat. No. 5,043,487 describes a process for the preparation of octadienols by reaction of 1,3-butadiene with water in the presence of a palladium compound and an optionally water-soluble, monodentate phosphine ligand, the addition of a triorganophosphine oxide and $CO_2$ being essential. In addition, the reaction requires an organic solvent.

Solvent-free reactions of butadiene and water in the presence of a palladium compound and a monodentate, water-soluble phosphine ligand, such as, for example, sodium trisulfnatophosphine (TPPTS) are described in U.S. Pat. Nos. 5,345,007 and 4,142,060.

The reaction in U.S. Pat. No. 5,345,007 requires the addition of a tertiary amine or a quaternary ammonium compound containing a long-chain alkyl radical, e.g. dimethyldodecylamine or cetyltrimethylammonium hydroxide, under a $CO_2$ pressure of 10 bar.

The object of the present invention is to provide an improved, economically favorable process for the telomerization of dienes using a compound containing an active hydrogen atom, which process gives the corresponding products in high yield and purity and permits simple isolation of the products. In particular, it is the object of the invention to provide a process of this type which can be used to convert butadiene into 2,7-octadienol in high yield and selectivity.

According to the invention, this object is achieved by a process, according to which the diene is reacted with a compound containing an active hydrogen atom in the presence of a palladium compound, a water-soluble phosphine ligand, a base and water, the water-soluble phosphine ligand being a bidentate ligand having the following formula (I)

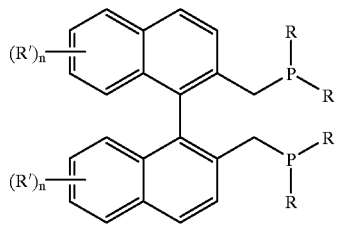

I in which

R is identical or different and is phenyl, $C_1$–$C_{12}$-alkyl or $C_3$–$C_{10}$-cycloalkyl, which may be unsubstituted or substituted by one or more radicals R', R' is identical or different and is $SO_3^-M^+$, —$NMe_3^+$ or —$COO^-M^+$, n is an integer from 1 to 6, in each case based on a naphthyl backbone, and M is H, Na, K, Cs or $R''_4N^+$ where R" is identical or different and is H, $C_1$–$C_{12}$-alkyl or $C_3$–$C_{10}$-cycloalkyl.

For the process according to the invention, particularly suitable compounds of the formula I are compounds in which the total number of R' groups is n*=from 2 to 28, in particular n*=from 3 to 10, particularly preferably n*=from 4 to 8, in each case based on the overall molecule, compounds where $R'=M^+SO_3^-$ being very particularly preferred.

An example of a particularly preferred ligand I (BINAS=sulfonated II,II'-bis(diphenylphosphinomethyl)-1,1'-binaphthalene) is shown in FIG. II.

Figure II

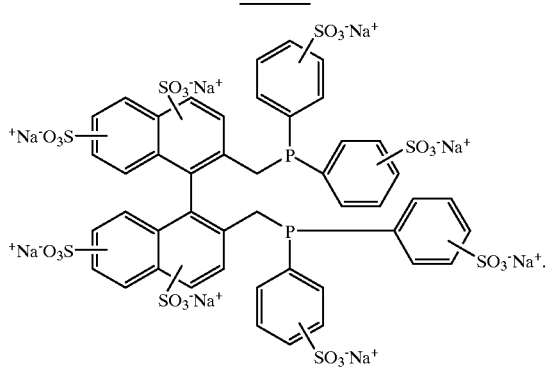

The bidentate biphenylphosphine ligands I used according to the invention may, in general terms, be obtained by sulfonation of the parent substance with oleum. A process for the preparation is described, for example, in W. A. Herrmann et al., Angew. Chem., 1995, 107, 893.

The process according to the invention does not require the addition of organic auxiliaries such as the amines or triorganophosphine compounds used in the prior art. In addition, the process according to the invention has the advantage that when, for example, water is used as the compound containing an active hydrogen, the reaction does not require an additional organic solvent.

Palladium compounds which may be used are Pd(0) complex compounds and Pd(11) compounds. Suitable examples are palladium acetates, halides, nitrites, carbonates, ketonates, acetylacetonates, nitrile palladium halides, olefinpalladium halides, allylpalladium halides and palladium biscarboxylates.

Specific examples are, for example, $Pd(OAc)_2$, $Pd(acac)_2$, $(CH_3CN)_2Pd(NO_2)Cl$, $(C_{10}H_8N_2)PdCl_2$,$Pd_2(dba)_3$ and $PdCl_2$.

Surprisingly, good results have also been obtained with $PdCl_2$, although it had been described that palladium chloride hinders the dimerization (Tsuji, J. Moni, Y.; Tetrahedron. 1972, 28, 3721).

For the process according to the invention, the ligand can be used in customary amounts generally known to persons skilled in the art, based on the amount of palladium compound. The molar ratio of ligand to palladium compound is preferably from 1 to 50, in particular from 1 to 10 and, very particularly preferably, from 2 to 6.

For the process according to the invention, the palladium compound is used in an amount of $10^{-3}$–10 mol %, preferably $5 \times 10^2$–5 mol % and, particularly preferably, $10^{-2}$–1 mol %, based on the diene.

Dienes suitable for the process according to the invention are preferably aliphatic dienes having from 4 to 8, in particular from 4 to 6, carbon atoms.

Particularly preferred dienes are conjugated ones such as butadiene, 1,3-pentadiene and isoprene.

The compound containing an active hydrogen atom can be water, alcohols ROH where R=$C_1$–$C_8$, phenols, amines and acids such as organic carboxylic acids.

Examples of alcohols are primary, saturated or unsaturated, straight-chain or branched aliphatic alcohols having, preferably, from 1 to 10 carbon atoms, and the corresponding aliphatic and alicyclic secondary alcohols having, preferably, from 3 to 10 carbon atoms. Preferred examples thereof are MeOH, EtOH, BuOH, i-PrOH, cyclohexanol and allyl alcohol.

Examples of amines are primary or secondary, aliphatic alkylamines having $C_1$–$C_8$-alkyl chains, such as methylamine, ethylamine, dimethylamine and diethylamine.

For the process according to the invention, particular preference is given to the compounds containing an active hydrogen atom which can simultaneously act as solvent in the reaction, i.e. telomerization, meaning that an additional organic solvent is not necessary. Examples thereof are, in particular, water and MeOH.

Thus, the process according to the invention is particularly effective for the telomerization of butadiene with water, since the industrially important 2,7-octadienol can be obtained in high yield and selectivity in a simple manner without the addition of organic solvents and organic compounds as auxiliaries.

If required, it is, however, possible to add to the reaction mixture a suitable organic solvent which is inert toward the constituents of the reaction mixture.

Examples thereof are dimethyl sulfoxide, sulfolane, dimethylformamide, acetonitrile, acetone, toluene, benzonitrile or, for example, an ether such as dimethyl ether, diethylene glycol and dimethoxyethane.

The process according to the invention is carried out in the presence of bases. Examples of bases which are preferentially used are the hydroxides of the alkali metals and alkaline earth metals, and also amines, particular preference being given to NaOH and KOH due to their ready availability.

For the process according to the invention, the base is preferably used in an amount of from 0.1 to 10 mol %, particularly preferably from 0.3 to 5 mol % and very particularly preferably 14 mol %, based on the diene.

For the process according to the invention, it is furthermore advantageous to add a carbonate and/or hydrogencarbonate compound or a mixture thereof. Suitable examples are the corresponding alkali metal or alkaline earth metal compounds.

For the process according to the invention, the amounts of this carbonate or hydrogencarbonate compound or of mixtures thereof are usually the same as those given above for the base.

Particularly preferred examples of these carbonate and hydrogencarbonate compounds are the sodium and potassium compounds.

In a preferred embodiment, the process according to the invention is carried out under an inert-gas atmosphere, e.g. under argon or nitrogen.

To carry out the process according to the invention, the diene, a catalytic amount of the palladium compound, the bidentate phosphine ligand I, the base, optionally at least one carbonate and/or hydrogencarbonate compound and optionally an organic solvent can be initially introduced into a suitable reaction vessel, e.g. an autoclave, preferably under an inert-gas atmosphere. If necessary, the initial charging takes place with cooling. The reaction preferably takes place with stirring or shaking.

The diene can also be added to the reaction system only once the catalyst mixture has been prepared.

If the diene is gaseous, as is the case for butadiene, it can be added in the condensed state.

The reaction mixture is then brought to the desired reaction temperature and left to react, preferably with stirring. When the reaction is complete, the reaction mixture is, if necessary, brought to the ambient conditions. The reaction preferably takes place at a temperature of from 50 to 100° C., in particular from 70 to 90° C. If the temperature is lower than 50° C., the reaction proceeds too slowly; if the temperature exceeds 100° C., undesired secondary reactions may occur.

The reaction can be carried out batchwise or continuously.

The process according to the invention can proceed under the autogenous pressure of the reaction.

The reaction mixture is worked up using customary methods familiar to the person skilled in the art, e.g. distilling off the excess diene and distilling the products. The catalyst which remains may, if desired, be reused. In the case of two-phase reaction mixtures, after the reaction is complete, the organic phase (telomer) can be readily separated off from the aqueous phase containing the catalyst.

In a particularly preferred process according to the invention, the palladium compound and the bidentate phosphine ligand I are initially introduced into a vessel. NaOH and, preferably, $Na_2CO_3$, dissolved in water, are added thereto.

Another vessel is charged with optionally condensed butadiene. The catalyst mixture is added to an autoclave flushed with inert gas.

The butadiene is then added.

The reaction takes place at elevated temperature, preferably at 70–90° C., over several hours, preferably 2–4 hours.

The reaction mixture is then cooled to room temperature or slightly above, and the unreacted butadiene is transferred to a vessel cooled to $-78°$ C. The organic phase is separated off from the reaction mixture, cooled to room temperature, and the desired product is isolated from said organic phase by a conventional method such as, for example, distillation.

This process can be used to obtain 2,7-octadienol in high yield and good selectivity in a simple manner without the addition of other solvents or auxiliaries. The process according to the invention is illustrated in more detail by reference to illustrative examples, although it is not limited thereto.

EXAMPLES 1 to 5

A Schlenk apparatus was charged with $Pd(OAC)_2$ (336.8 mg, 1.5 mmol), which was dissolved in DMSO (1.7 ml, 23.7 mmol). BINAS (43.6 mg, 6 mmol) was added to the solution, as a result of which an exothermic reaction (30° C.) was observed. $Na_2CO_3$ (795 mg, 7.5 mmol) and NaOH (900 mg, 22.5 mmol), which were dissolved in $H_2O$ (18 ml, 1000 mmol) were added to this mixture, and the resulting mixture was cooled to $-15°$ C. Another Schlenk apparatus, which had been cooled to $-78°$ C., was charged with butadiene (714 mmol).

A 250 ml autoclave was cooled to $-78°$ C. and flushed with $N_2$.

Under $N_2$, the catalyst mixture and then the butadiene were added to the autoclave. The autoclave was closed, and firstly heated to room temperature and then to 90° C.

After 4 hours with stirring at 90° C., the reaction mixture was cooled to 50° C., and the unreacted butadiene was transferred via a valve to a Schlenk apparatus cooled to $-78°$ C., in order to recover the unreacted butadiene.

The autoclave was then cooled to room temperature and emptied. The resulting organic phase was separated off and analyzed by gas chromatography. This reaction was carried out in the same way for different palladium compounds.

The results given in the table below were obtained:

Example

| | Pd compound | 2,7-Octadienol | 1,7-Octadien-3-ol | Vinylcyclohexene + 1,3,7-octatriene |
|---|---|---|---|---|
| 1 | $Pd(OAc)_2$ | 64.1 | 13.3 | 7.0 |
| 2 | $Pd(acac)_2$ | 63.9 | 11.2 | 6.4 |
| 3 | $(CH_3CN)_2Pd(NO_2)Cl$ | 63.5 | 12.1 | 7.6 |
| 4 | $(C_{10}H_8N_2)PdCl_2$ | 59.2 | 13.9 | 8.5 |
| 5 | $PdCl_2$ | 64.9 | 10.0 | 7.2 |

(All yield data in % by weight)

The reminder were pounds which were not identified more specifically.

EXAMPLE 6 and COMPARATIVE EXAMPLE

The procedure was as given in Examples 1 to 5, the Pd compound being $Pd(OAc)_2$ and the ligand being BINAS or sodium trisulfonatophosphine (TPPTS), a monodentate ligand. The reaction conditions were 80° C. and 16 hours. The resulting organic phase was analyzed by gas chromatography, the results given below being obtained:

| | 2,7-Octadienol | 1,7-Octadien-3-ol | Vinylcyclohexene + 1,3,7-octatriene | |
|---|---|---|---|---|
| BINAS | 70% | 12% | 9% | (E6) |
| TPPTS | 46% | 14% | 11% | (CE) |

(All yield data in % by weight)

The remainder were compounds which were not identified more specifically.

Because water was used both as a compound having an active hydrogen atom and as a solvent, all of the examples according to the invention and the comparative example produced a two-phase reaction mixture in which the organic phase (telomer) was distinct from the aqueous catalyst phase and could therefore be readily separated off.

What is claimed is:

1. A process for the telomerization of dienes, which comprises reacting the diene with a compound containing an active hydrogen atom in the presence of a palladium compound, a water-soluble phosphine ligand, a base and water, wherein the water-soluble phosphine ligand is a bidentate ligand having the formula I

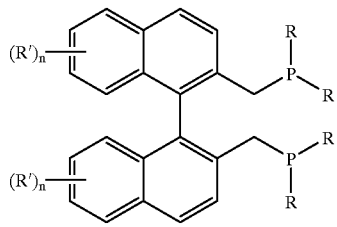

I in which

R is identical or different and is phenyl, $C_1$–$C_{12}$-alkyl or $C_3$–$C_{10}$-cycloalkyl, which may be unsubstituted or substituted by one or more radicals R', R' is identical or different and is $SO_3^-M^+$, —$NMe_3^+$ or —$COO^-M^+$, n is an integer from 1 to 6, in each case based on a naphthyl backbone, and M is H, Na, K, Cs or $R''_4N^+$ where R" is identical or different and is H, $C_1$–$C_{12}$-alkyl or $C_1$–$C_{10}$-cycloalkyl.

2. The process as claimed in claim 1, where the total number of R' groups is n*=from 2 to 28, based on the overall molecule.

3. The process as claimed in claim 1, where the bidentate phosphine ligand I is a ligand having the following formula

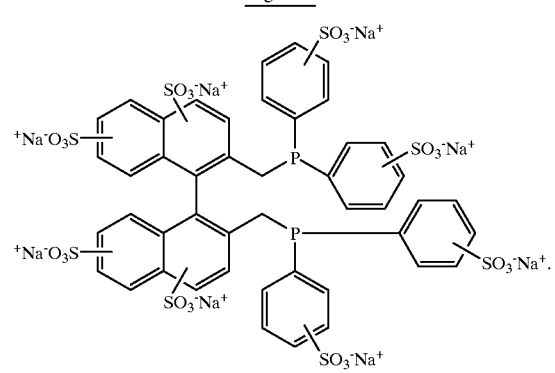

Figure II

4. The process as claimed in claim 1, where the palladium compound is chosen from palladium acetates, halides, nitrites, carbonates, ketonates, acetylketonates, nitrile palladium halides, olefinpalladium halides, allylpalladium halides and palladium biscarboxylates.

5. The process as claimed in claim 4, where the palladium compound is chosen from $Pd(OAc)_2$, $Pd(acac)_2$, $(CH_3CN)_2Pd(NO_2)Cl$, $(C_{10}H_8N_2)PdCl_2$, $Pd_2(dba)_3$ and $PdCl_2$.

6. The process as claimed in claim 1, where the diene is chosen from aliphatic dienes having from 4 to 8 carbon atoms.

7. The process as claimed in claim 6, where the diene is a conjugated diene.

8. The process as claimed in claim 7, where the diene is chosen from butadiene, 1,3-pentadiene and isoprene.

9. The process as claimed in claim 1, where the compound containing an active hydrogen atom is chosen from water, $C_1$–$C_8$-alcohols, phenols, amines and acids.

10. The process as claimed in claim 9, where the compound containing an active hydrogen atom is chosen from water and MeOH.

11. The process as claimed in claim 1, where the base is chosen from an alkali metal hydroxide, alkaline earth metal hydroxide and an amine.

12. The process as claimed in claim 11, where the base is NaOH or KOH.

13. The process as claimed in claim 11, where the base is used in an amount of from 0.1 to 10 mol %, based on the diene.

14. The process as claimed in claim 1, where at least one compound chosen from carbonate and hydrogencarbonate compounds and mixtures thereof is additionally added to the reaction mixture.

15. The process as claimed in claim 14, where the compound is a sodium or potassium salt.

16. The process as claimed in claim 14, where the compound is added in an amount of from 0.1 to 10 mol %, based on the diene.

17. The process as claimed in one of the preceding claims, where the reaction takes place at a temperature chosen from the range from 50° C. to 100° C.

18. The process as claimed in claim 17, where the temperature is chosen from a range from 70° C. to 90° C.

19. The process as claimed in claim 1, where the process is carried out under an inert-gas atmosphere.

20. The process as claimed in claim 1 wherein the total number of $R^1$ groups (n*) in the overall molecule is from 3 to 10.

21. A process for the preparation of di-n-octyl phthalate which comprises:

1) reacting butadiene and water in the presence of a palladium compound, a water-soluble phosphine ligand and a base, wherein the water soluble phosphate ligand is a bidentate ligand of the formula

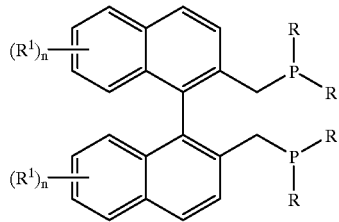

I in which

R is identical or different and is phenyl, $C_1$–$C_{12}$-alkyl or $C_3$–$C_{10}$-cycloalkyl, which may be unsubstituted or substituted by one or more radicals R', R' is identical or different and is $SO_3^-M^+$, —$NMe_3^+$ or —$COO^-\ M^+$, n is an integer from 1 to 6, in each case based on a naphthyl backbone, and M is H, Na, K, Cs or $R''_4N^+$ where R'' is identical or different and is H, $C_1$–$C_{12}$-alkyl or $C_1$–$C_{10}$-cycloalkyl;

2) hydrogenating the 2,7-octadienol obtained in step 1 to produce 1-octanol; and 3) resulting 1-octanol with phthalic anhydride to produce reacting the di-n-octyl phthalate.

* * * * *